United States Patent [19]

Hancock et al.

[11] Patent Number: 4,466,746
[45] Date of Patent: Aug. 21, 1984

[54] EBULLIOMETRIC HOT SPOT DETECTOR

[75] Inventors: Robert D. Hancock, 475 Lakeshore Dr., Chrystal Bay Cove, Unit 32, Incline Village, Nev. 89450; Kenneth F. Hollman, San Marcos, Calif.

[73] Assignee: Robert D. Hancock, Incline Village, Nev.

[21] Appl. No.: 326,224

[22] Filed: Dec. 1, 1981

[51] Int. Cl.³ ............................................. G01N 25/72
[52] U.S. Cl. .......................................... 374/5; 324/52; 324/73 PC; 324/158 R
[58] Field of Search ................. 324/52, 73 PC, 158 F, 324/158 R; 374/4, 5, 24, 27, 100, 159

[56] References Cited

U.S. PATENT DOCUMENTS

| | | | |
|---|---|---|---|
| 2,578,265 | 12/1951 | Saalfrank | 103/152 |
| 3,361,037 | 1/1968 | Likavec | 92/37 |
| 3,396,335 | 8/1968 | Burr et al. | 324/51 |
| 3,510,762 | 5/1970 | Leslie | 324/52 |

OTHER PUBLICATIONS

Blackburn, D. L., "An Electrical Technique for the Measurement of the Peak Junction Temperature of Power Transistors," *Proc. IEEE 13th Annual Conf. on Reliability Physics* (1975), pp. 142–150.
Brenner, D. J., "A Technique for Measuring the Surface Temperature of Transistors by Means of Fluorescent Phosphor," *N.B.S. Technical Note* 591 (1971), pp. 1–46.
Anon., "Determining Hot Spots, Temperatures on IC Chips," *Circuits Manufacturing* (Sep. 1976).
Dandon, G. P., "A Cheap Way to Detect Failure Sites on LSI Devices Using Fluorocarbon," *Semiconductor International '80*, Brighton, Eng. (1980) (Abstract).
Cole, R., "Homogeneous and Heterogeneous Nucleation," In: Van Stralen, S. and Cole, R., *Boiling Phenomena*, N.Y., McGraw-Hill, 1979, vol. I, pp. 71–73.

*Primary Examiner*—Herbert Goldstein
*Attorney, Agent, or Firm*—Fitch, Even, Tabin & Flannery

[57] ABSTRACT

An ebulliometric hot spot detector detects hot spots with a resolution of the order of a micron on semiconductor devices. The device to be tested is operated in a suitable liquid contained in the detector, and the liquid pressure is decreased until boiling from sites on the device is observed. The liquid pressure is then increased until boiling ceases; meanwhile, the boiling sites on the device are observed. Small bubbles observed just before cessation of boiling pinpoint the hot spot locations. The pressure at which boiling ceases in a given liquid determines the hot spot temperature.

22 Claims, 28 Drawing Figures

Microfiche Appendix Included
(1 Microfiche, 62 Pages)

FIG. 3
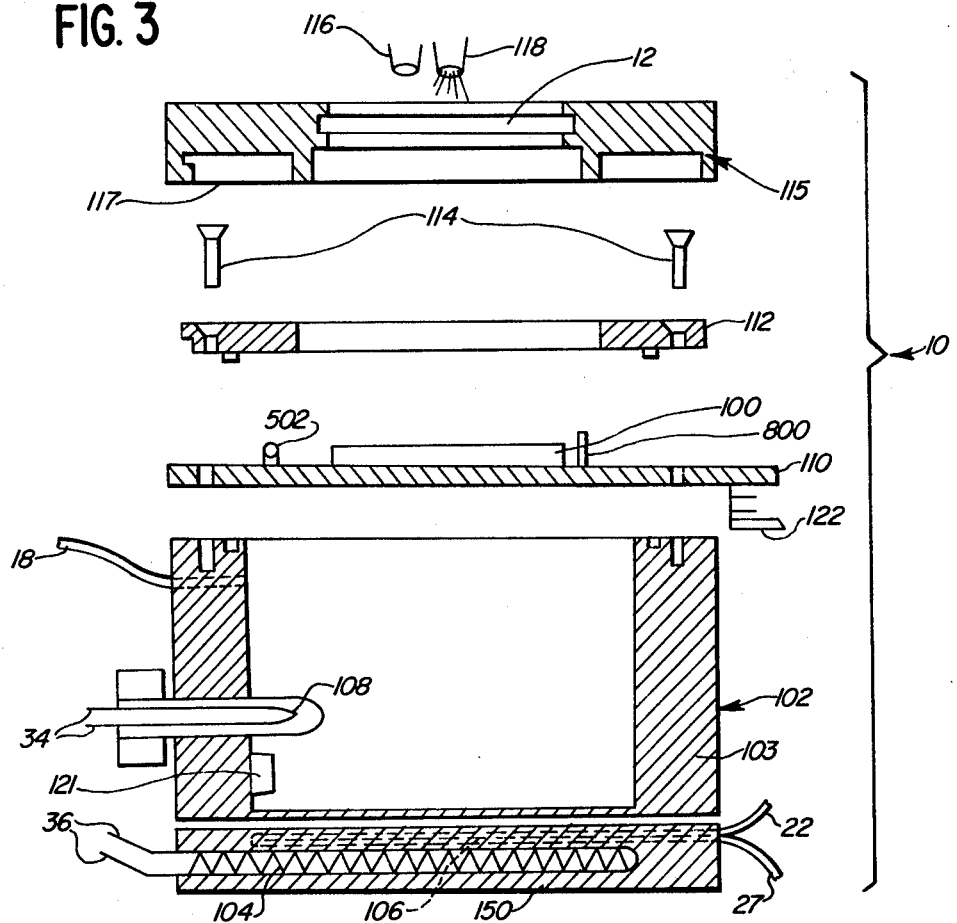
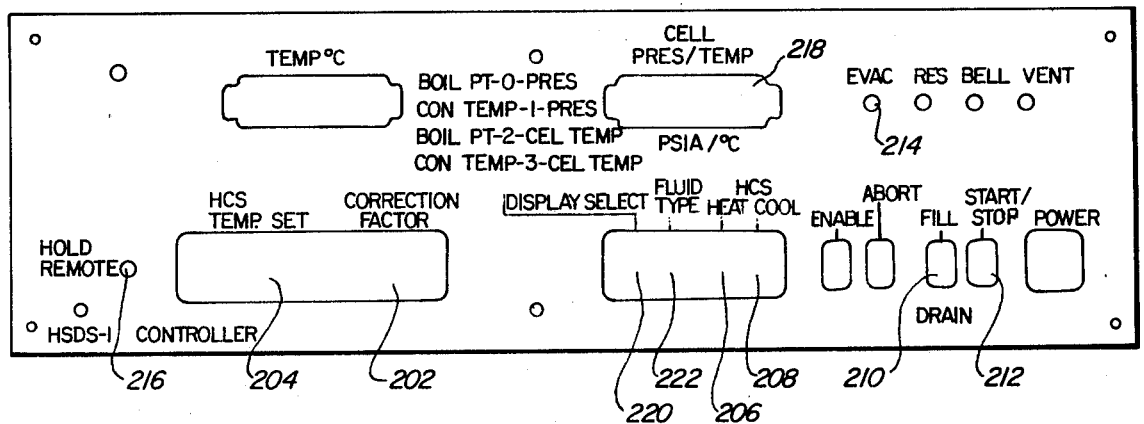
FIG. 4

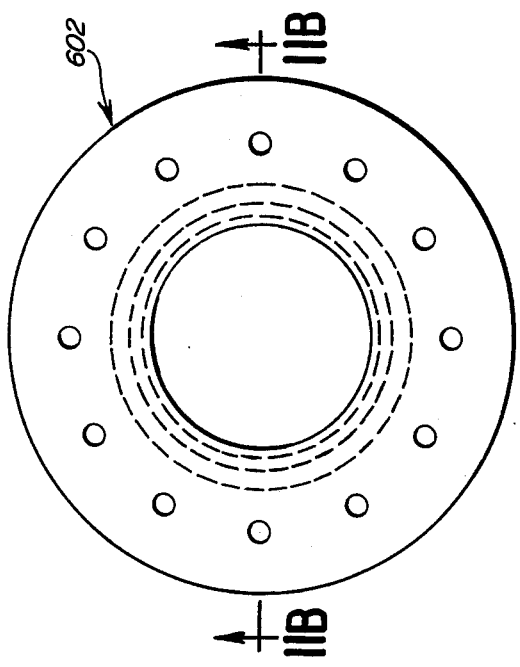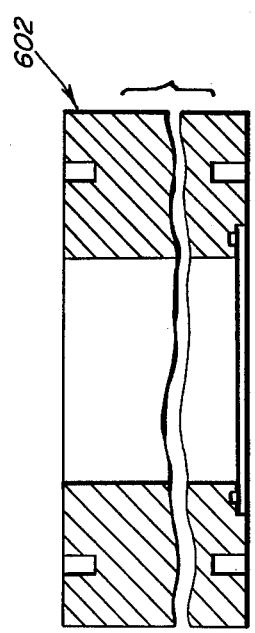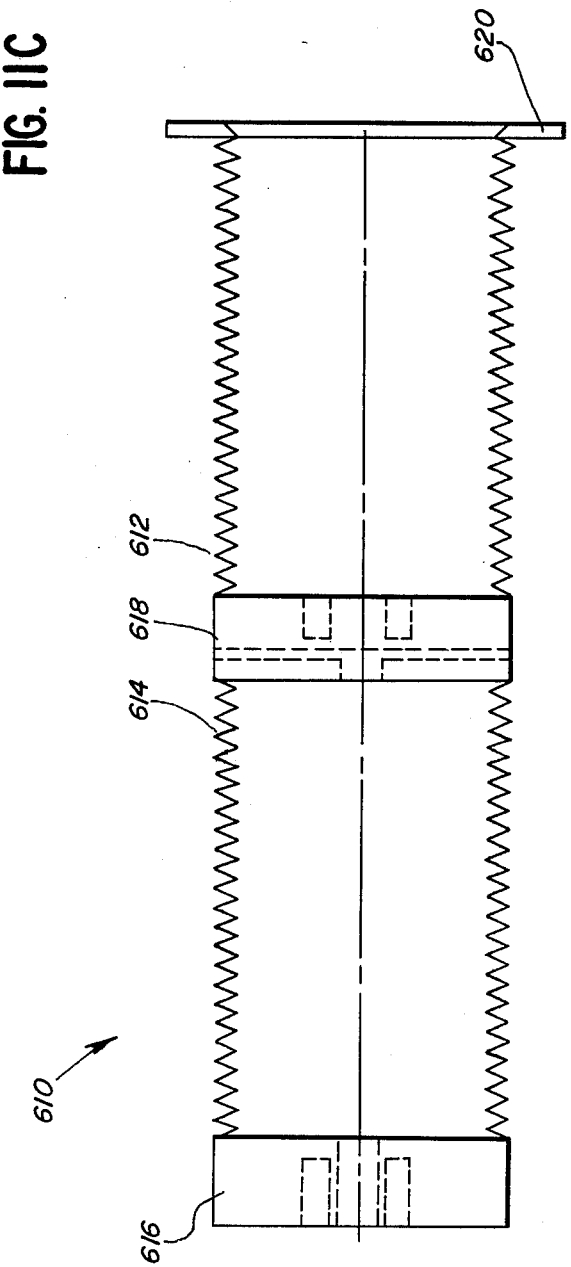

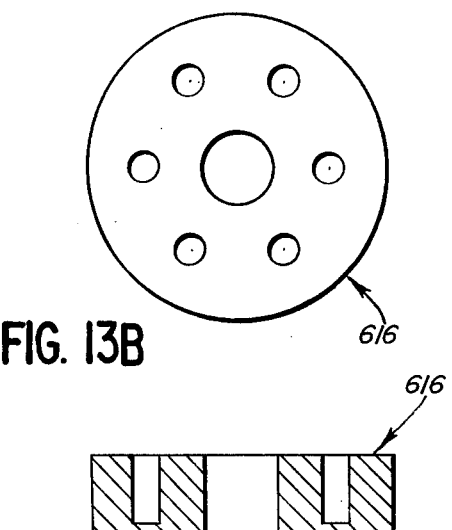
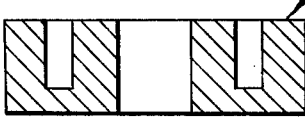
FIG. 13B
FIG. 13A
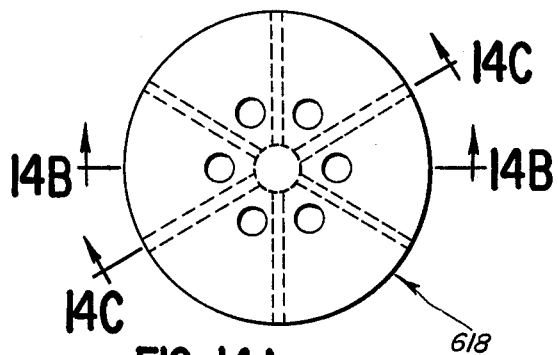
FIG. 14A
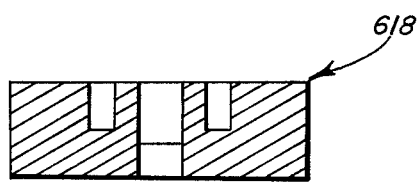
FIG. 14B
FIG. 15A
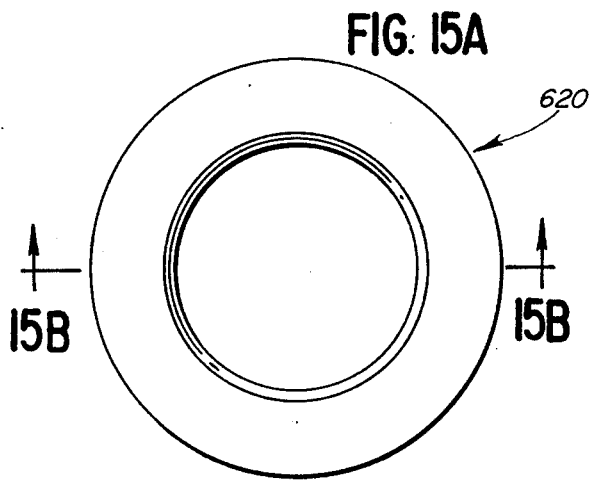
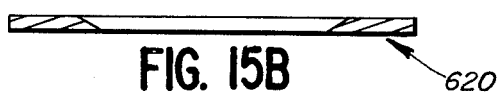
FIG. 15B
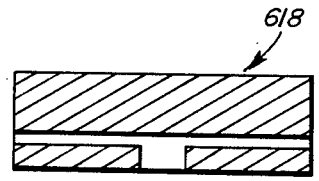
FIG. 14C
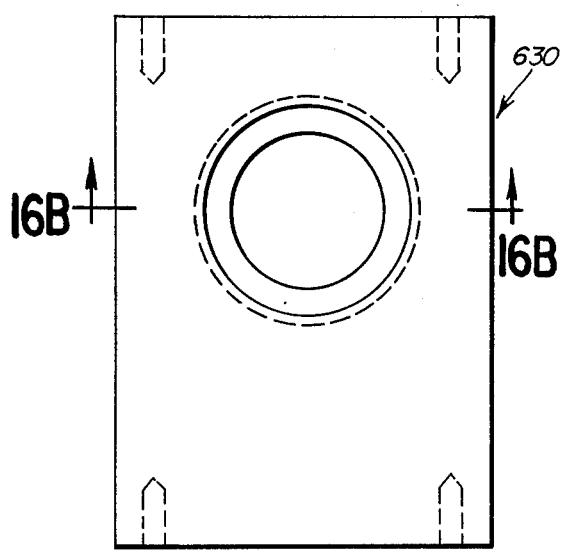
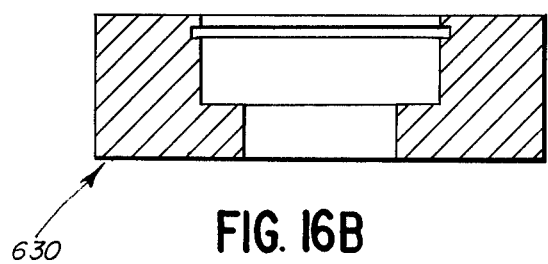
FIG. 16B
FIG. 16A

EBULLIOMETRIC HOT SPOT DETECTOR

Filed with this application is a Microfiche Appendix, containing microcomputer program listings. The Appendix contains 62 microfiche in one frame.

CROSS-REFERENCES

This application is related to a concurrently executed and filed U.S. application by the same inventors entitled Method and Apparatus for Ebulliometric Measurements, filed Dec. 1, 1981 as Ser. No. 326,274.

BACKGROUND OF THE INVENTION

This invention relates generally to ebulliometry. More particularly, this invention relates to an ebulliometric technique for detecting localized hot spots on small objects, such as integrated circuits.

Operating microelectronic devices may have highly nonuniform temperature distributions resulting mainly from ohmic heating. The nonuniform distributions may result in localized hot spots which induce early failures of the devices. On printed circuit boards, for example, localized heating may result from defects in metallizing, such as excessive metal etching or poor plate-through connections, which in turn cause the current carrying area to be insufficient under load. Poor heat sink design and inadequate solder connections may also result in localized heating of printed circuit boards. Localized heating causes hot spots and related failure problems. Integrated circuits are subject to troubles similar to those which may afflict printed circuit boards.

Detection of hot spots, particularly in integrated circuits, becomes increasingly difficult as the size scales of the circuits decrease.

Prior art techniques for detecting hot spots are discussed in Blackburn, "An Electrical Technique for the Measurement of the Peak Junction Temperature of Power Transistors," *Proc. IEEE* 13th *Annual Conf. on Reliability Physics* (1975), and Brenner, "A Technique for Measuring the Surface Temperature of Transistors by Means of Fluorescent Phosphor," *National Bureau of Standards Technical Note* 591 (1971).

One prior art method of locating hot spots is the scanning infrared microscope. This device detects the infrared radiation emitted from electronic circuits under test. Infrared detection systems are complex, expensive, and difficult to use. Further, they are not suitable for use with large scale integrated circuits because of the inherent resolving power limitations of infrared systems. An infrared detection system can only resolve emission regions having sizes of the order of the wave length of the detected radiation, or greater. For example, a modern high quality infrared microscope, discussed in Barnes Engineering Co. Bulletin 12-910C, having a spectral response of about 1.8 to 5.5 microns can resolve emitting regions greater than about 7.6 microns diameter. Present-day semiconductor devices very often have structures which are less than one micron in size; these structures cannot be resolved under an infrared microscope.

Infrared detection of hot spots is also not conducive to the determination of absolute hot spot temperatures because of the dependence of the infrared radiation upon the emissivity of the radiating region. A semiconductor device has a number of materials with different emissivities such as bare silicon, silicon oxide, metallized conductors, and passivating glass. Present practice, therefore, is to coat a device with black lacquer in order to obtain uniform emissivity. The coating, however, obscures the view of the precise structure of the device under test. Also, the coating, being a good radiator, alters the thermal characteristics of the device, thereby making quantitative interpretation of measurements difficult. When coatings are not used, metallized conductors may be particularly troublesome because the conductors act as mirrors and give false indications of hot spots by generating reflections from nearby light sources.

Brenner describes a technique for the determination of hot spot temperatures by coating a transistor chip with a temperature-sensitive phosphor. The phosphor's fluorescence when irradiated by ultraviolet light of suitable intensity is strongly temperature-dependent. Brenner mounted the coated chips on a temperature-controlled heat sink and applied various voltages to the chip. The fluorescent pattern was photographed through an enlarging lens and the film analyzed with a microdensitometer to extract temperature data.

Brenner's technique is not useable for devices having connecting wires obscuring the surfaces, heavy metallization, or external coatings or packaging. The resolution is limited by the phosphor grain size which can occur in clumps up to 50 microns in diameter. The phosphor coating technique is therefore unsuitable for hot spot detection on integrated circuits having structures with sizes of the order of a micron or less.

Another known technique described in "Determining Hot Spots, Temperatures on IC Chips," *Circuits Manufacturing* (September 1976), involves placing a device on a thermoelectric element which is cooled to a temperature below the condensation temperature of nitrogen gas saturated with a fluorocarbon liquid. The saturated gas is blown across the device until the fluorocarbon forms a condensation layer on the device surface. Power is then applied to the device until hot spots exhibit themselves as breaks in the condensation layer. The surface temperature of a hot spot at any given power input is determined by cooling the thermoelectric element to a second temperature at which condensation on the hot spot recurs. It is assumed that the difference between the temperatures of the hot spot and thermoelectric device is essentially independent of the thermoelectric device temperature. The hot spot temperature at any ambient temperature is therefore assumed to be the temperature difference between the ambient and second thermoelectric element temperatures plus the condensation temperature of the fluorocarbon liquid. Observations of the breaks in the condensation layer and the subsequent recondensation are made through a microscope.

One difficulty in the condensation technique is that it does not reveal hot spots which are not directly in the field of view of the microscope. Thus, it may be necessary to observe a device from many aspects in order to obtain complete coverage for hot spot detection. Another difficulty is that tests are limited to device temperatures in the range of about 0° C. to 70° C. It would be desirable to be able to test over a much greater temperature range. Finally, hot spot resolution is limited by surface tension effects and is probably not better than several microns.

More recent work, some of which is described by G. P. Dunden, *Semiconductor International* '80, Brighton, England (1980), involves immersion of a device in a fluorocarbon liquid. Hot spots manifest themselves as boiling sites. The technique has been used to detect hot spots on printed circuit, multi-layered and wire wrap boards. The technique has not previously given good results for integrated circuits because the bubbles emitted from hot spots disturb the fluid surface, making it difficult to see individual boiling sites and otherwise obscuring the view of the boiling sites. The technique is in any event limited to the detection of hot spots having temperatures above the boiling point of the particular liquid used. The boiling technique has not been applied to hot spot temperature determination.

SUMMARY OF THE INVENTION

The present invention relates to the determination of the location and temperature of hot spots in electronic circuitry. An embodiment of the invention may make use of a liquid which boils at the site of a hot spot, thereby marking the location of the hot spot. The boiling temperature of the liquid is then increased by increasing the pressure of the liquid until boiling ceases, in order to determine accurately the temperature of the hot spot.

A preferred embodiment will avoid spurious boiling point determinations resulting from superheating of the liquid before nucleate boiling occurs, as discussed, e.g., in Van Stralen and Cole, *Boiling Phenomena*, Vol. 1, p. 71, (McGraw-Hill, 1979). Liquid superheating may occur when the temperature of a liquid at substantially fixed pressure is increased from a temperature below the boiling point. It has been observed that the liquid may reach a temperature many degrees above its boiling point before the onset of nucleate boiling. When nucleate boiling begins and the liquid pressure is subsequently increased, the size of the bubbles associated with boiling is observed to decrease until bubble formation stops. The pressure and temperature at which bubble formation just terminates is substantially the boiling point of the liquid.

Observations made in connection with the present invention show that just prior to the cessation of boiling in fluorocarbons such as hexafluoroethane, for example, bubbles of about 1 micron diameter are observed. When the heat source is highly localized, therefore, its location may be determined to within a fraction of a bubble diameter, that is, within a fraction of a micron.

An apparatus constructed in accordance with the present invention may comprise a pressure test cell or bubble cauldron filled with a clean fluid having a known relationship between boiling temperature and pressure. A device to be tested, connected for operation, is immersed in the fluid and the pressure of the fluid reduced until boiling is detected. The pressure is then increased, causing the size of the vapor bubbles involved in the boiling process to decrease. When the produced bubbles are in approximately the one micron range, the boiling site or sites are determined with precision. The pressure is then increased, and the pressure at which boiling terminates is noted.

The pressure at which boiling just terminates in a pressure test cell may be referred to as the ebulliometric pressure for the fluid at the temperature of the hottest hot spot device on the device under test.

A microprocessor controlled thermocouple hot spot, which in a specific construction has been named a "whirligig", is heated while the pressure in the cauldron is held constant at the previously determined ebulliometric pressure. When boiling is detected from the hot spot on the whirligig the temperature of the whirligig hot spot is then slowly decreased under microprocessor control until the highest temperature at which boiling stops is observed. The observed temperature may be referred to as the ebulliometric temperature corresponding to the pressure in the cauldron. The temperature of the hottest hot spot on the device is thereby determined. Conversion tables available to the microprocessor then permit the microprocessor to provide the hot spot temperature in air corresponding to the hot spot temperature determined in the fluid. Alternatively, the whirligig may be operated in air at the same value of power input as at the cessation of boiling in liquid to approximate the hot spot temperature in air.

Fluids usable for hot spot detection with semiconductor devices and printed circuits, which may be referred to as "ebulliometric" fluids or liquids, must have low boiling points and be electrically nonconductive. Additional desirable characteristics are low toxicity and substantial nonflammability for ease and a safety of handling, and a low dielectric constant to provide minimal interference with the electrical operation of a device under test resulting from the capacitance between the device and the testing vessel. All of the desirable properties are found in fluorocarbons such as the perfluorinated hydrocarbons hexafluoroethane and octofluoropropane. The following "R" compounds, which may be purchased under the Freon and Genetron labels, have been found useful for application to hot spot detection: R-13, R-13B1, R-114, R-500 and R-502.

The boiling points of fluids are increased by contaminants. It is therefore necessary to provide means for varying fluid pressure without contaminating the liquid used in the hot spot detector. One construction of the present invention used a positive displacement bellows pump to vary pressures ranging from negative gauge pressures to substantially in excess of 1000 psi without contaminating the liquid.

It is, accordingly, an object of the present invention to provide nondestructive determinations of positions and temperatures of localized hot spots on the surfaces of printed circuits, IC wafers, chips, transistors, and other electronic devices by the detection of ebulliometric phenomena at the sites of the hot spots.

It is also an object of the present invention to provide for the detection of ebulliometric phenomena in high dielectric strength fluorocarbon liquid by optical, acoustical and other nondestructive techniques.

It is a further object of the present invention to provide a bubble cauldron test chamber usable for determining the location and temperature of hot spots in electronic devices. These and other objects, features, and advantages of the invention will be apparent from the following description of a specific construction of the preferred embodiment as illustrated in the accompanying drawings.

DESCRIPTION OF THE DRAWINGS

FIG. 3 is an exploded cross-sectional view of the bubble cauldron shown in FIG. 2, taken along line 3—3 in FIG. 2;

FIG. 4 is a front elevation of a control panel of the microprocessor/controller shown diagrammatically in FIG. 1;

FIG. 6A is a side elevation of the device shown in FIG. 6 illustrating a bubble field above a hot spot;

FIGS. 11A, 11B, and 11C are, respectively, side horizontal sectional and end views of the housing of the bellows displacement pump assembly shown in FIG. 7, FIG. 11B being a section taken along line 11B—11B in FIG. 11C;

FIG. 12 is a side view of the bellows assembly of the bellows displacement pump shown in FIG. 7;

FIGS. 13A and 13B are, respectively, a horizontal axial sectional view and an end view of the stainless steel plug of the bellows assembly shown in FIG. 8;

FIGS. 14A, 14B and 14C are, respectively, an end view and sectional views taken along lines 14B—14B and 14C—14C of FIG. 14A of the piston of the bellows assembly shown in FIG. 8;

FIGS. 15A and 15B are, respectively, an end view and horizontal sectional view taken along line 15B—15B of FIG. 15A of the annulus of the bellows assembly shown in FIG. 8;

FIGS. 16A and 16B are, respectively, an end view and a horizontal sectional view taken along line 16B—16B of FIG. 16A of a pillow block shown in FIG. 7;

DETAILED DESCRIPTION OF THE SPECIFIC CONSTRUCTION OF A PREFERRED EMBODIMENT

System Description

Figures 1, 2:
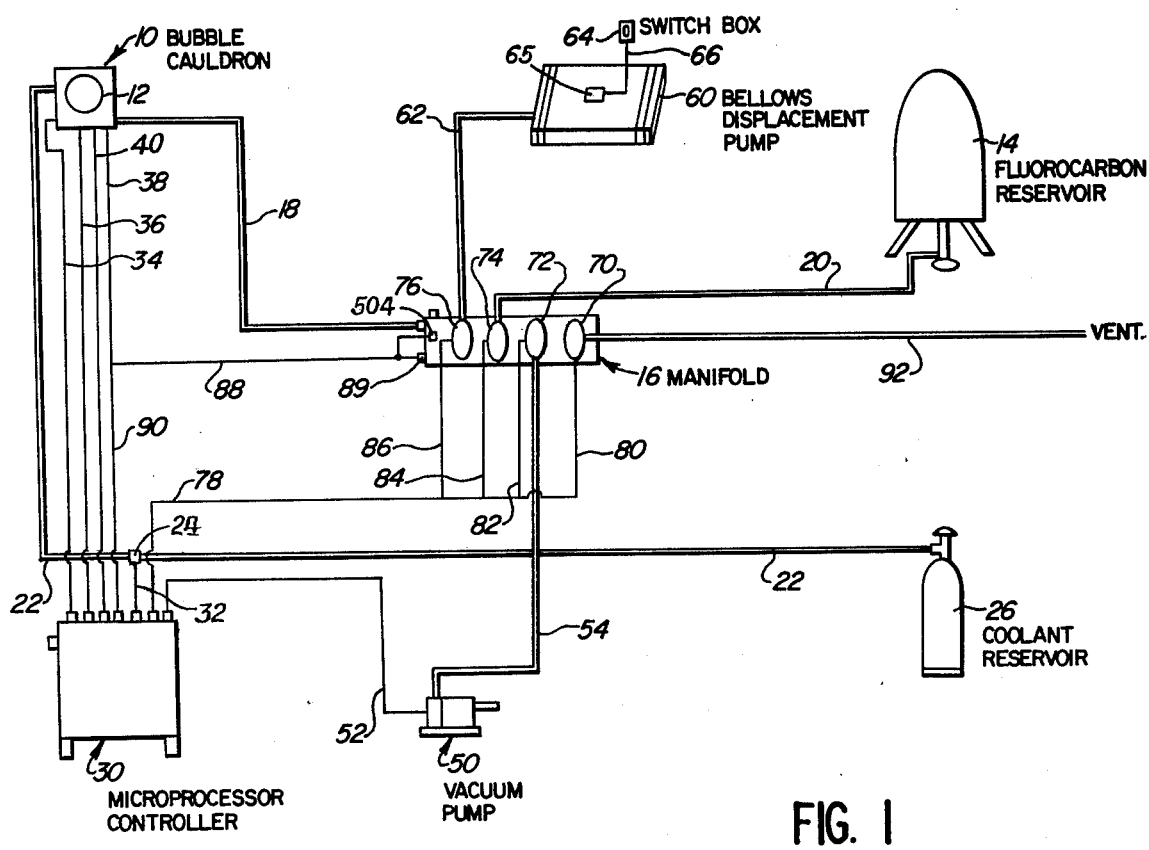
FIG. 1 is a diagrammatic illustration of a specific construction of a hot spot detector built in accordance with the principles of the present invention.
FIG. 2 is a plan view of a bubble cauldron as used in the hot spot detector shown in FIG. 1, illustrating a device under test and a whirligig as they would be seen through a bubble cauldron window.

As illustrated in FIG. 1, a specific construction of a preferred embodiment of a hot spot detector comprises a bubble cauldron 10 with an optically clear window 12. The bubble cauldron 10 is connected to a fluorocarbon reservoir 14 through a multivalve manifold 16. A fluorocarbon transfer line 18 connects the manifold 16 to the bubble cauldron 10. A fluorocarbon fill line 20 connects the fluorocarbon reservoir 14 to the manifold 16. A coolant fluid transfer line 22 feeds through a microprocessor controlled coolant solenoid valve 24 to a coolant reservoir 26. In one construction of a preferred embodiment the coolant fluid may comprise liquid $CO_2$.

A microprocessor/controller 30 is connected to the coolant solenoid valve 24 by a coolant control bus 32. The microprocessor/controller 30 is also connected to the cauldron 10 by thermocouple leads 34, heating coil leads 36, and sensing and control leads 38. A roughing vacuum pump 50 is activated by control leads 52 from the microprocessor/controller 30. The vacuum pump 50 is connected to the manifold 16 by a vacuum line 54. A bellows displacement pump 60, to be described in detail, is connected to the manifold 16 by a pressure line 62. The displacement pump 60 is controlled by a remote switch 64 connected to a displacement pump motor 65 by a remote lead 66.

The multivalve manifold 16 includes four ports having solenoid controlled valves. A first port 70 vents to the atmosphere. A second port 72 connects to the vacuum line 54. A third port 74 connects to the fluorocarbon fill line 20. The fourth port 76 connects to the pressure line 62. A solenoid bus 78 from the microprocessor/controller 30 includes lines 80, 82, 84, and 86 controlling, respectively, the solenoids at the ports 70, 72, 74, and 76. Lines 88 include transducer lines connecting a pressure transducer 89 within the manifold 16 to the microprocessor/controller 30 by way of a sensing bus 90. The sensing and control leads 38 and the transducer line 88 connect to the microprocessor/controller 30 through a sense bus 90. A vent 92 from the first port 70 provides for venting the manifold 16 to the atmosphere.

FIG. 2 shows a plan view of the bubble cauldron 10 with a device 100 being tested for hot spots shown in place. The view shown is through the optically clear window 12. FIG. 3 shows an exploded cross-sectional view of the bubble cauldron 10.

As may be seen most clearly in FIG. 3, the bubble cauldron 10 comprises a main chamber 102, which may be formed by an aluminum drum 103 about 1.9" height and 3⅜" diameter, open at its top end and enclosing a cylindrical chamber about 1.4" high and 2¼" in diameter. The drum 103 is made of conducting metal in a preferred embodiment for ease of heating and cooling the chamber's contents. The drum 103, and in fact the entire structure to be described, must be sufficiently strong to withstand pressures to be applied to the contents of the bubble cauldron 10. The drum 103 may be made to rest upon a separate base 150 in which heating coils 104 may be embedded with heater current leads 36 projecting from the side of the base 150 and connecting to an external current source in the microprocessor/controller 30. Similarly, cooling coils 106 may be embedded in the base 150 and connected to the coolant fluid transfer line 22 and to a coolant gas vent 27. A thermocouple junction 108 is provided in the interior of the main chamber 102 with means for passing the thermocouple leads 34 through the chamber wall while preserving the pressure integrity of the wall.

A printed circuit board 110 adapted for use with the bubble cauldron 10 fits snugly over the top of the main chamber 102. Apertures are provided in the circuit board to provide for the free flow of liquid from the main chamber into the region above the circuit board. Means such as socket connectors are provided on the upper face of the printed circuit board for rapid connection of a device 100 which is indicated diagrammatically in FIG. 3. An annular seal 112 mounts above the printed circuit board 110 so that the printed circuit board 110 fits between the annular seal 112 and the top of the drum 103. The annular seal 112 is secured to the drum 103 by screws 114 which pass through the printed circuit board 110 into the top of the wall of the drum 103. Pressure-tight seals are thereby provided where the annular seal 112, printed circuit board 110, and the top of the drum 103 make contact. A top lid 115 containing the optically clear window 12 fits snugly over the annular seal 112 so that the optically clear window 12 fits directly above the device 110 under test, the optically clear window being substantially parallel to the printed circuit board 110. The device 100 under test is substantially centered with respect to the circular perimeter of the main chamber 102 and also with respect to the optically clear window 12. The underside 117 of the top lid 115 may be made attachable to the drum 103 by rapid attachment means such as a bayonet type fitting.

A microscope or other viewing means 116 and a light source 118, as diagrammatically indicated in FIG. 3, may be placed directly above the optically clear window 12 for viewing. One variation of the specific construction described herein includes means 121 for applying pressure pulses to the fluid in the bubble cauldron 10 during viewing as indicated schematically in FIG. 3. Mixing means for insuring thermal mixing may also be associated with means 121. The pressure pulses may be used to move convection plumes obscuring the view of the device 100 under test through the viewing means 116. A part of the printed circuit board 110 projects beyond the periphery of the drum 103 and provides ribbon connectors 122 for making electronic connections to the printed circuit board 110 and thence to the device 100 under test.

Means are also provided for connecting the fluid transfer line 18 to the main chamber 102 for filling the bubble cauldron 10 with fluorocarbon fluid as is indicated in FIG. 2.

In addition to the device 100 under test, a whirligig thermocouple/heating element 130 is also placed within the field of view of the microscope 116 and may be conveniently placed upon the circuit board 110. The whirligig thermocouple/heating element 130 is described in detail in the concurrently filed related application. Located on the whirligig thermocouple 130 is a hot spot 132 indicated schematically in FIG. 2. Ribbon leads 134 may be mounted on the printed circuit board 110 to provide for electrical connections to the whirligig 130. A control plane, displayed schematically in FIG. 4, is provided on the microprocessor/controller 30.

Figure 5:
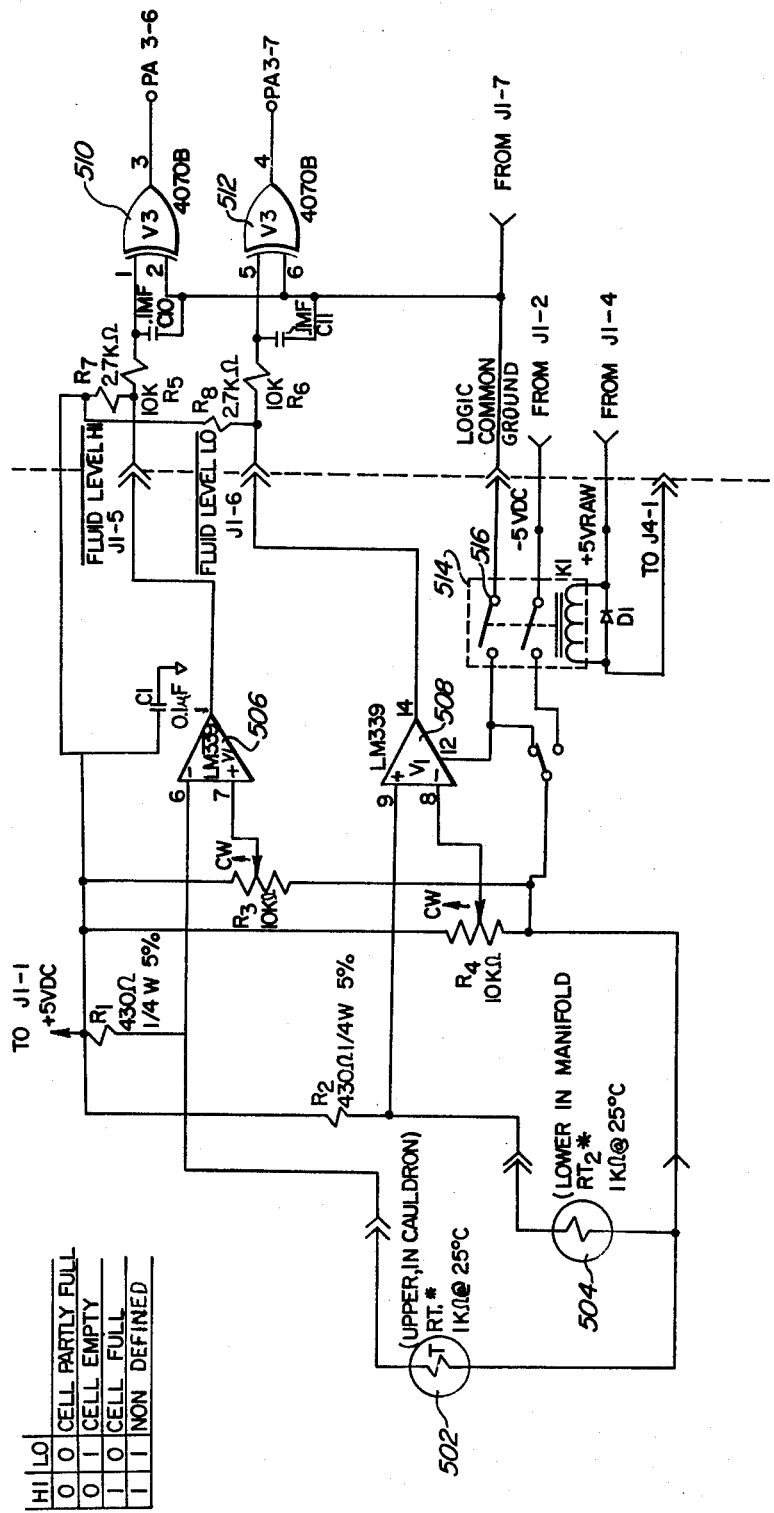
FIG. 5 is a circuit diagram of a thermistor level sensor as used in the hot spot detector illustrated in FIG. 1.

First and second thermistors 502, 504, shown in FIG. 5, are used to indicate fluid level. The first thermistor 502 is mounted on top of the printed circuit board 110 as shown in FIGS. 2 and 3 and is connected to the microprocessor/controller 30 over the sensing and control lines 38 which connect to the sensing bus 90. The second thermistor 504 is located in the manifold and connects to the microprocessor/controller 30 over the lines 88 which also connect with the sensing bus 90.

The thermistor circuitry is illustrated in FIG. 5. One terminal of each thermistor is connected to a 5 volt DC voltage source through a respective 430 ohm resistor R1, R2. The same terminal of the first thermistor 502 connects directly to the inverting input of a first op-amp 506. The corresponding terminal of the thermistor 504 is connected directly to the noninverting terminal 508-9 of a second op-amp 508. The op-amps may comprise LM339 op-amps as shown in FIG. 5. The remaining terminals of the two thermistors 502, 504 are tied together and connected to the 5-volt source through a pair of parallel 10 K-ohm potentiometers R3 and R4.

The noninverting terminal 506-7 of the first op-amp 506 and the inverting terminal 508-8 of the second op-amp 508 are connected respectively to the taps of the potentiometers R3 and R4. The thermistors may be Fenwall thermistors GB31L1 available from Fenwall Electronics, Framingham, MA 01701, as used in the specific construction described herein. The op-amps 506, 508 are used as comparators, and their outputs connect respectively through 10 K-ohm resistors R5 and R6 to inputs 510-1, 512-5 of exclusive OR-gates 510, 512. The remaining inputs 510-2 and 512-6 are tied together and connected to the logic common ground as shown in FIG. 5.

The outputs of the op-amps 506-1 and 508-14 are connected to the 5-volt DC source respectively through resistors R7 and R8, each having a resistance of 2.7 K-ohms. The connections through R7 and R8 provide for high outputs from the exclusive OR-gates 510 and 512 when the level sensor is off. A pair of capacitors C10 and C11 connect the inputs 510-1 and 512-5 to logical ground, thereby providing debounce circuitry that is effective when the level sensor is switched on and off. A pin J4-1 connects to a Darlington driver which is controlled by the microprocessor/controller 30. When the driver is enabled, an unfiltered +5 v raw source from a pin J1-4 is applied to a relay 514 as shown in FIG. 5. Current in the relay 514 closes a switch 516 to apply power to the op-amps 506 and 508 and to energize the thermistors 502 and 504.

The potentiometers R3 and R4 are set generally so that the threshold for the respective op-amps 506, 508 to change state is approximately halfway between the self-heating temperature of the thermistors 502, 504 and the temperature of the bath surrounding the thermistors when the manifold 16 and cauldron 10 are filled. Fluid in the manifold 16 will normally be at room temperature; the potentiometer R4 will therefore normally be set so that the op-amp 508 will transition when the thermistor temperature is approximately 43° C. The fluid in the cauldron 10, on the other hand, will have temperatures lying in the range 16° C. to 33° C. It is convenient, therfore, to set the op-amp 506 so that it transitions at a thermistor temperature of approximately 40° C. In operation, the presence of fluid around the thermistors 502 and 504 will cause the thermistor temperatures to drop, thereby increasing the resistances of the respective thermistors. When the resistance of thermistor 502 increases, the op-amp input 506-6 voltage rises. When the voltage on the op-amp input pin 506-6 increases about the reference voltage at pin 506-7, the output at output pin 506-1 drops low, causing the exclusive OR-gate 510 to output a low on pin 510-3. Persons skilled in the electronics art will appreciate that the first exclusive OR-gate will output a low when there is fluid in the cauldron 10. The second exclusive OR-gate 512 will output a low when there is no fluid in the manifold 16. The signals from the exclusive OR-gates 510 and 512 are fed to the microprocessor/controller 30 and sensed thereby.

Figure 7:
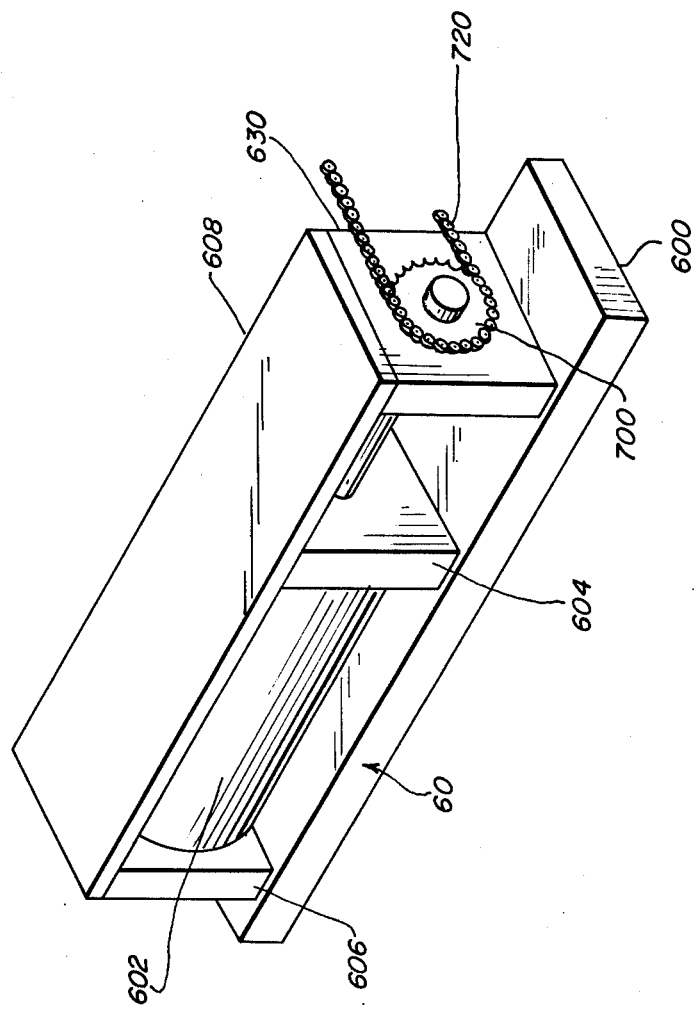
FIG. 7 is an isometric view of a bellows displacement pump shown diagrammatically in FIG. 1.

The bellows displacement pump 60 is shown in FIG. 7. The pump 60 may be used to obtain pressures ranging from a few psi negative gauge pressure to a few hundred psi without appreciably contaminating the ebulliometric liquid. A base plate 600 may comprise a piece of aluminum stock having dimensions approximately $\frac{1}{2}'' \times 19'' \times 22''$. An aluminum housing 602 is mounted between first and second end plates 604, 606, as shown in more detail in FIG. 8.

The end plates 604, 606, shown in more detail in FIGS. 9A and 9B, and 10A and 10B respectively, may each be fashioned from $\frac{1}{4}''\times 3\frac{1}{2}''\times 4\frac{1}{4}''$ aluminum plates. Each of the plates 604, 606 is screw-connected along one of its $3\frac{1}{2}''$ edges to the base plate 600, thereby defining the bottom edges of the plates 604, 606. In the specific construction described herein, the end plate 606 is mounted about $\frac{5}{8}''$ from, and parallel to, one end of the base plate 600, the $\frac{5}{8}''$ being measured along the longest dimension of the base plate 600. The $3\frac{1}{2}''$ dimension of the end plate 606 is approximately centered with respect to the 19'' dimension of the base plate 600.

The plates 604, 606 are mounted having the $3\frac{1}{2}''\times 4\frac{1}{4}''$ faces of the plates parallel, with approximately 6'' spacing between the nearest faces to accommodate the housing 602.

As shown in FIGS. 9A, 9B, 10A and 10B, each plate is drilled with the 0.690'' diameter hole centered between the edges along the $3\frac{1}{2}''$ dimension of the plate and $1\frac{3}{4}''$ from the top. An inner circle of six holes centered on a diamter of 1.4'' is placed symmetrically and concentrically about the 0.690'' hole. These holes are tapped in the plate 604. An outer ring of 12 holes centered on a circle of approximately 2.7'' is also spaced symmetrically and concentrically about the 0.690'' hole. The 3.5'' top and bottom edges are each tapped with a pair of screw holes symmetrically placed approximately 2.7'' apart. The screw holes on the bottom edges of the rear plate 604 and front plate 606 are used for screw mounting to the base plate 600.

Figure 11A:
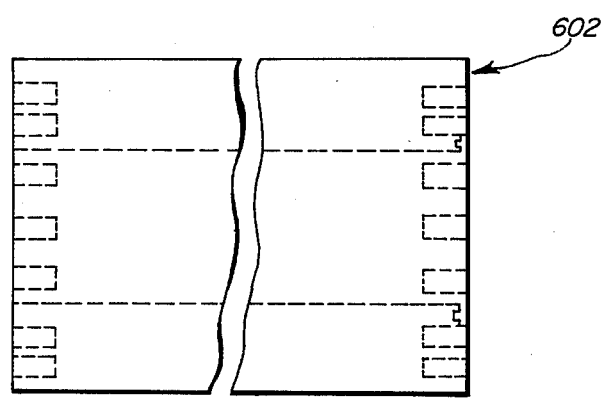

FIGS. 11A, 11B and 11C show, respectively, side, horizontal cross-sectional, and end views of the housing 602, which is essentially a cylindrical aluminum tube approximately 6'' long, $3\frac{1}{2}''$ outer diameter, and 1.72'' inner diameter. The ends of the housing 602 are tapped for screw mounting to the holes in the plates 604, 606 provided in the 2.7'' diameter circle about the 0.690'' holes.

Figure 8:
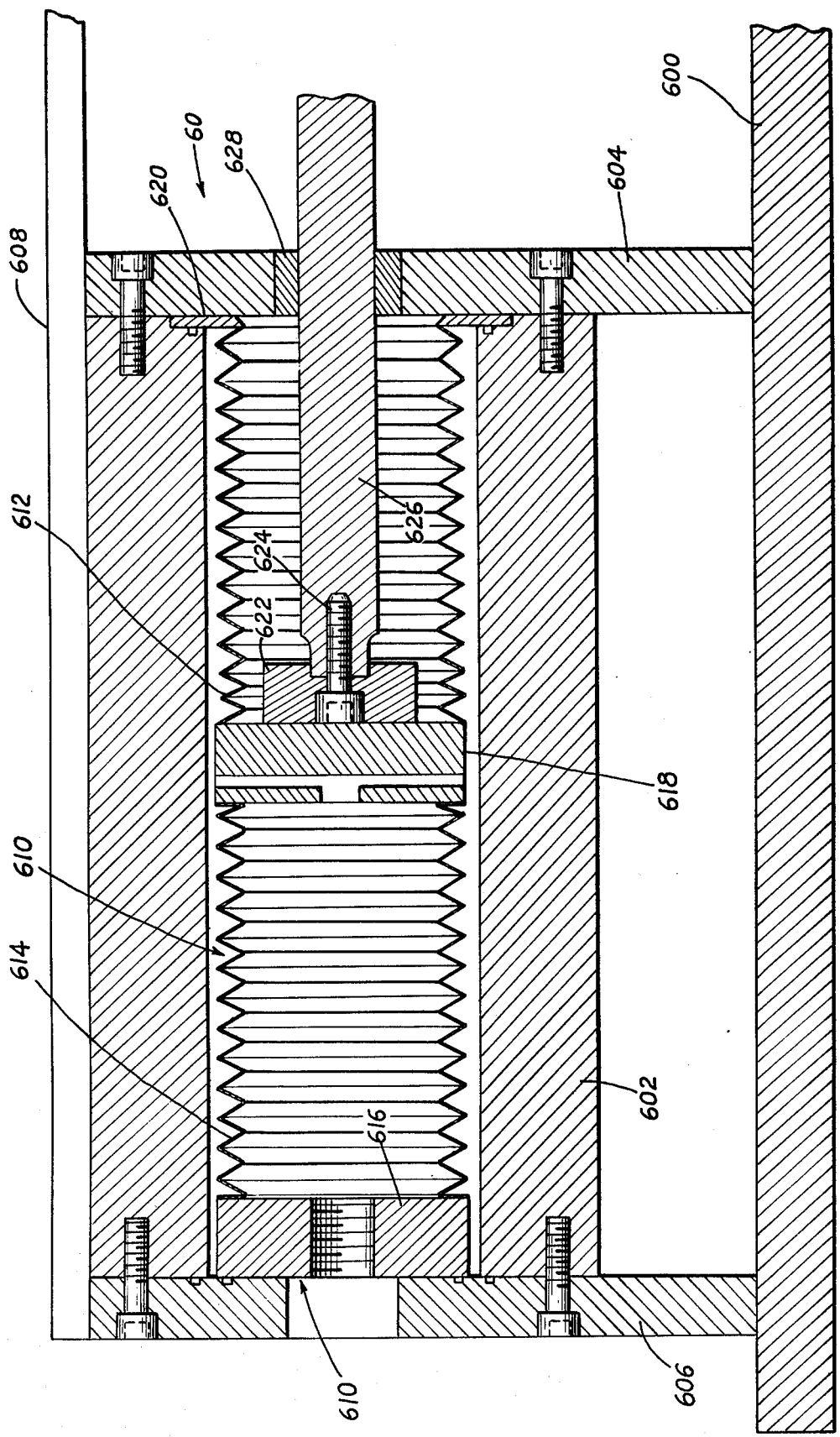
FIG. 8 is a vertical axial cross-sectional view of the bellows displacement pump illustrated in FIG. 7.
Figure 9B:
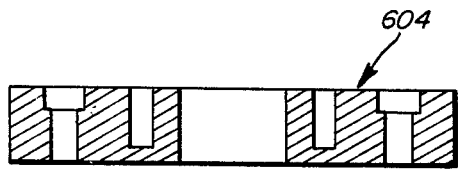
FIGS. 9A and 9B are, respectively, end and horizontal sectional views of one end plate of the bellows displacement pump shown in FIG. 7, FIG. 9B being a section taken along line 9B—9B in FIG. 9A.
Figure 10B:
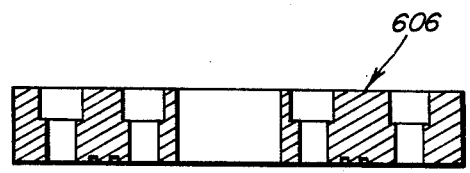
FIGS. 10A and 10B are, respectively, end and horizontal sectional views of the other end plate of the bellows displacement pump shown in FIG. 7, FIG. 10B being a section taken along line 10B—10B in FIG. 10A.
Figure 9A:
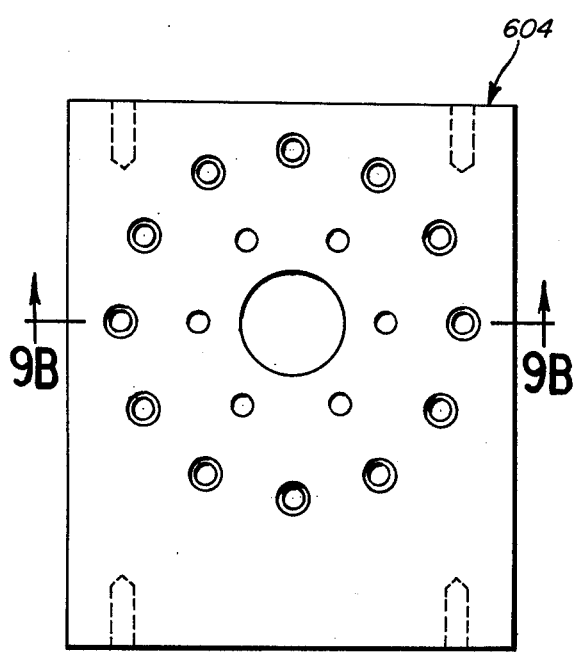
Figure 10A:
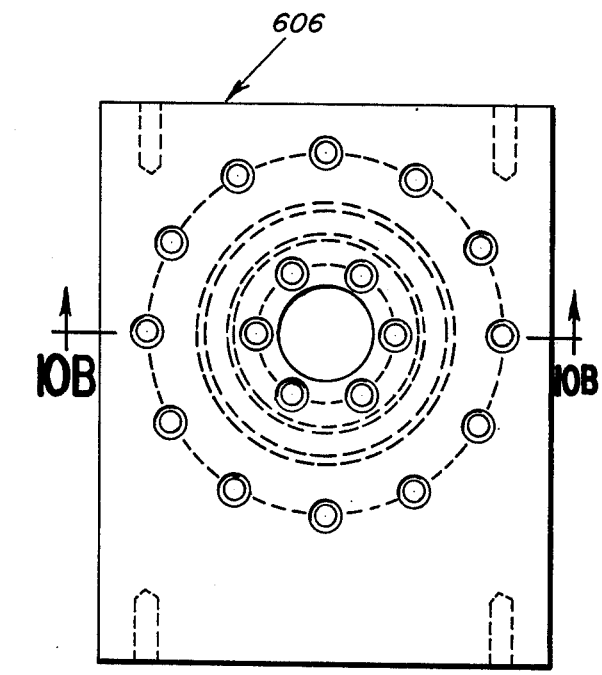

As shown in FIGS. 7 and 8, an aluminum top plate 608 approximately $\frac{1}{4}''\times 3\frac{1}{2}''\times 11\frac{1}{4}''$ is screw mounted to have one of its large faces flush with the top edges of the plates 604, 606. The top plate 608 may be placed to have one edge approximately flush with the large face of the plate 606 furthest from the plate 604 and also to be flush with the respective side edges of the plates 604, 606. An edge of the top plate 608 thereby projects approximately $4\frac{1}{4}''$ beyond the outermost face of the plate 604.

As shown in FIG. 8 and in more detail in FIG. 12, a welded bellows assembly 610 mounts within the housing 602. The bellows assembly comprises first and second bellows 612 and 614. Each of the bellows 612, 614 is manufactured from stainless steel bellows material approximately 0.006'' thick, with an outer diameter of approximately 1.62'' and an inner diameter of approximately 1.23''. Each of the bellows 612, 614 has a length of approximately 2.47''.

One end of the second bellows 614 is welded to the inner side of a stainless steel cylindrical plug 616 shown in more detail in FIGS. 13A and 13B. The plug 616 is center tapped along its axis with a cylindrical passage communicating between the ends of the plug 616, the passage having a diameter of approximately $\frac{3}{4}''$ and its axis substantially coincident with the axis of the plug 616. The outer face of the plug 616 has six threaded holes for screws centered on a circle having a diameter of 1.46'' centered on the axis of the plug. The plug diameter in the specific construction is 1.620'' and its thickness is 0.500''.

The other end of the bellows 614 is welded to the edge of a face of a stainless steel cylindrically-shaped piston 618 having a diameter of 1.620'' and a thickness of 0.500'' as shown in more detail in FIGS. 14A, 14B and 14C. As shown in FIGS. 14B and 14C, particularly, this face of the piston 618 is characterized by a cylindrical hole having an axis substantially coincident with the piston axis, a diameter of approximately $\frac{1}{4}''$, and extending 0.2275'' into the piston from such face. Also, as shown in more detail in FIGS. 14A and 14C, six radial passages having axes approximately 60° apart communicate from the center hole to the periphery of the piston and are located approximately 0.165'' behind such face. Six threaded holes are placed upon the other face of the piston, symmetrically centered on a circle of 0.625'' diameter centered on the piston axis. As may be seen in FIGS. 8 and 12, the six radial passages and center hole in the first face of the piston provide passages from the interior of the second bellows 614 to the exterior of the bellows assembly 610.

One end of the first bellows 612, terminating on the bellows outer diameter, is welded to the edge of the other face of the piston 618. The remaining end of the first bellows 612, terminating on its inner diameter, is welded to an inner diameter of a stainless steel annulus 620, shown in FIGS. 15A and 15B, having an outside diameter of 2.200'' and an inside diameter of 1.230''. The inner diameter of the annulus 620 is chamfered away from the welded joint at an angle of 45°, thereby defining the inner face of the annulus 620 as the face having the larger inside diameter. A first face of the housing 602 has a hole 2.200'' in diameter sunk approximately 0.060'', the hole being centered on the axis of the housing 602. An O-ring groove having a diameter of 1.907'' is formed symmetrically around the hole in the first face of the housing 602 as shown in FIGS. 11A and 11B.

The bellows assembly 610 is fastened to the inner side of the second plate 606 by screws connecting through the inner circle of six holes in the second plate 606 to the corresponding circle of six holes in the stainless steel plug 616 which is disposed to match the circle of holes in the second plate 606, substantially as shown in FIG. 8. The annulus 620 fits into the 2.200'' hole formed in the housing 602. The first plate 604 fits snugly against the first face of the housing 602 and the annulus 620 and is fastened to the housing by screws as described earlier. A cylindrical aluminum block 622 having a diameter of approximately 1.230'' and a thickness of approximately 3/16'' is screw-connected to the other face of the piston 618 utilizing the six screw holes shown in FIG. 14A. The axes of the block 622 and the piston 618 are made substantially coincident. A threaded screw 624 is sunk into the block to project approximately $\frac{3}{8}''$ beyond the block 622 in the direction away from the piston 618, the screw 624 being substantially centered upon the axis of the block.

One end of a $\frac{1}{2}''$ diameter steel shaft 626 is ground to the shape of a hexagon at one end. The center of the hexagonal end is tapped to receive the screw 624. The hexagonal end of the shaft 626 is pressfitted into a hole in the block 622 and then secured by the screw 624 as shown in FIG. 8, the hole having a diameter of 0.315''. The shaft 626 which is approximately $9\frac{1}{2}''$ long is threaded at its other end with 28 pitch threads. The shaft 626 passes concentrically through the central hole of the first plate 604. An Oil-Lite bushing 628 having an outer diameter substantially equal to 0.690'' and an inner diameter substantially equal to $\frac{1}{2}''$ provides a lubricated bearing surface for the shaft 626. In the specific construction described herein the Oil-Lite bushing 628 does not provide an airtight seal. The present invention also envisions modifications where the Oil-Lite bushing 628 is replaced by an airtight seal. The sealed version permits pressurization of the interior of the rear bellows 612, thereby permitting the attainment of higher pressures in the fluorocarbon fluid without increase of the forces applied to the shaft 626.

A pillow block 630, shown in FIGS. 16A and 16B, is made from a rectangular piece of aluminum stock approximately $1'' \times 3\frac{1}{2}'' \times 4\frac{1}{4}''$. The pillow block is screw-connected to the base plate 600 and top plate 608 with the $3\frac{1}{2}'' \times 4\frac{1}{4}''$ face substantially parallel to the outer face of the plate 604. The $3\frac{1}{2}''$ edges of the pillow block 630 contact the base plate 600 and top plate 608 with the outer face of the pillow block substantially flush with the end of the top plate 608. A 1.3" diameter hole having its center approximately 1.750" below the top of the pillow block 630 and substantially centered between the side edges of the pillow block 630 is drilled from the rear to the front of the pillow block.

Figure 17:
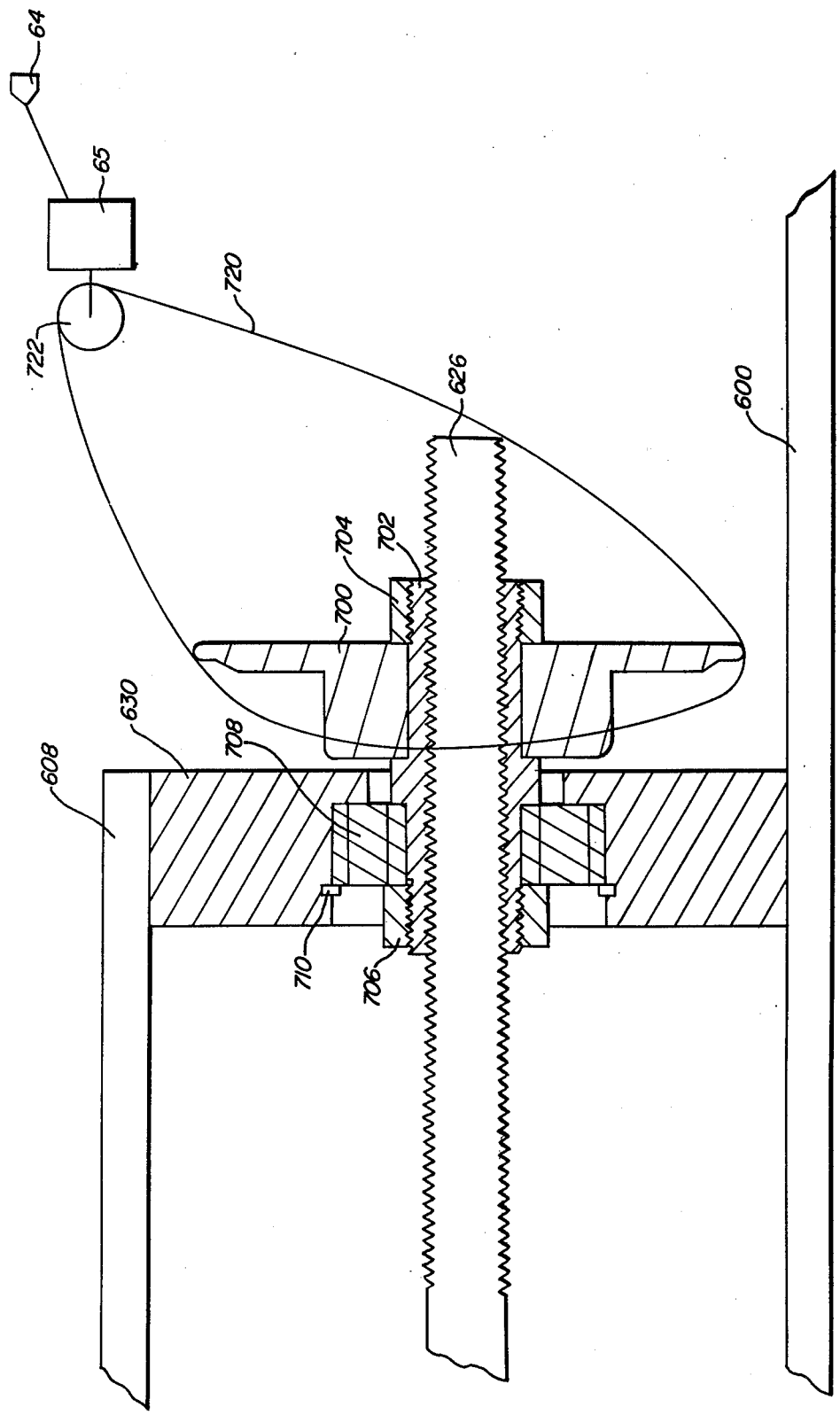
FIG. 17 is a vertical axial sectional view of the driving mechanism assembly for the bellows displacement pump shown in FIG. 7, also showing the motor and chain drive therefor diagrammatically.
Figure 18:
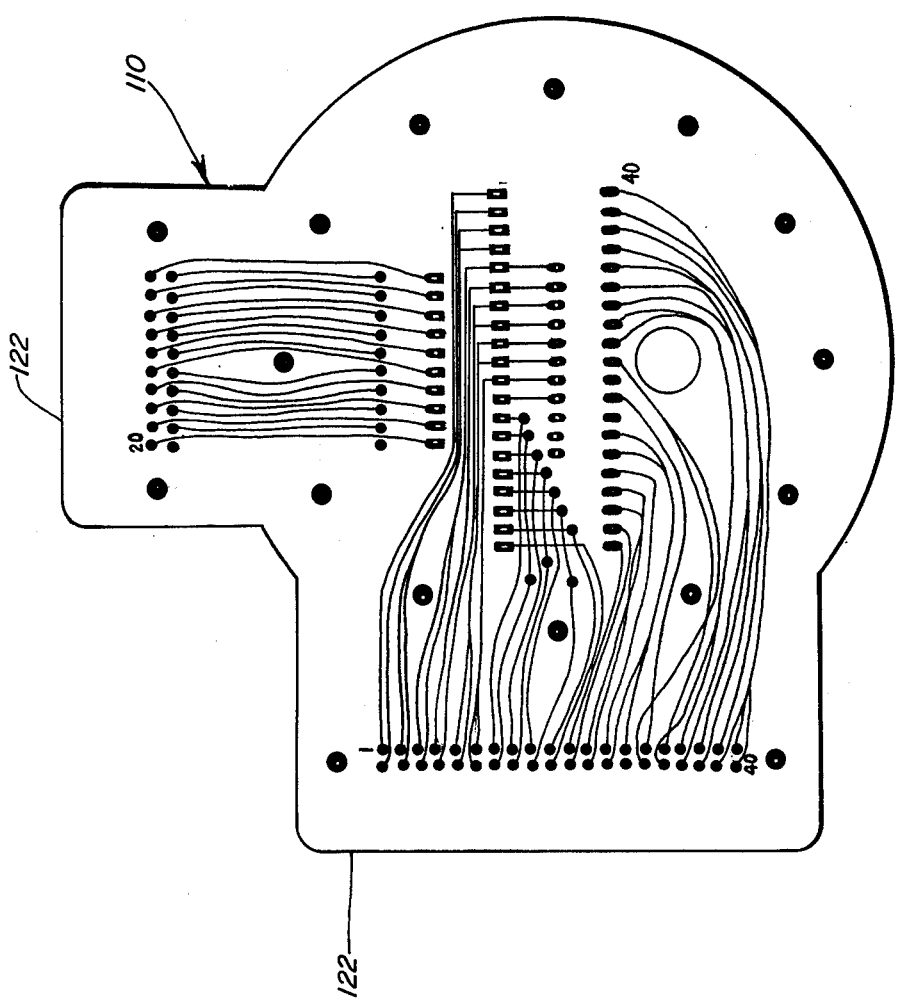
FIG. 18 is a plan view of the printed circuit board illustrated in FIG. 3.

As shown in FIG. 17, a sprocket 700 is rigidly attached to a shaft drive nut 702 and held in place by a first nut 704. A second nut 706 locks the shaft drive nut 702 against one face of a bearing 708. The bearing 708 is inserted into a receiving hole on one face of the pillow block 630, the receiving hole having a greater diameter and being concentric with the 1.3" diameter hole. The inner periphery of the shaft drive nut 702 is threaded to match the threaded end of the shaft 626 which is screwed into the shaft drive nut 702. One face of the bearing 708 rests against an inner face of the pillow block 630, the inner face terminating the receiving hole and being peripheral to the 1.3" diameter hole in the pillow block 630. The bearing 708 may be locked in place by a C-clip 710 in a suitably provided slot around the periphery of the receiving hole.

Rotation of the sprocket 700 drives the shaft 626 back and forth in a horizontal direction, thereby providing expansion and contraction of the bellows 612, 614. A chain 720 may be used to connect the sprocket 700 to a driving sprocket 722. The driving sprocket 722 may be rotated by driving means such as the stepping motor 65.

System Operation

Further understanding of the system is most easily achieved by describing system operation in accordance with Fairchild F6802 microprocessor program listings filed as a Microfiche Appendix to this application. According to one method of operation, the microprocessor/controller 30 memory contains data on properties of ten different fluorocarbon liquids. The fluorocarbon reservoir 14 is filled with one of the designated liquids prior to operation. A correction factor is then dialed into the microprocessor/controller 30 by a thumbwheel 202 on the control panel shown in FIG. 4. The correction factor is used by the microprocessor/controller 30 to correct hot spot temperatures measured in fluorocarbon liquid to equivalent air temperatures.

The operator may also select a bulk operating temperature between $-65°$ C. and $150°$ C. for the fluorocarbon and dial that into the microprocessor/controller 30 by a thumbwheel 204 on the face of the microprocessor/controller. The operator next turns on a heat switch 206 and a cool switch 208, sets a fill/drain switch 210 in the fill position, and puts a start/stop switch 212 in the start position to activate microprocessor control of system operation.

The microprocessor/controller 30 first transmits a signal over the vacuum pump control line 52 to initiate operation of the vacuum pump 50, concurrently activating the solenoid control line 82 to open the port 72 from the manifold 16 to the vacuum pump and turning on an EVAC light 214. The vacuum pump 50, operating as a roughing pump, reduces the pressure in the exhaust manifold 16 and chamber 102 to a pressure of 3-5 mm Hg. The actual pressure is preselected in the microprocessor memory and is not critical as long as it is less than about 10 mm Hg. The microprocessor/controller 30 monitors the pressure in the manifold over the lines 88 from the pressure transducer 89.

The microprocessor/controller 30 causes the solenoid valve 24 in the coolant line 22 to open, concurrently with vacuum pump operation, to permit coolant to flow into the cooling system of the bubble cauldron 10 and exhaust to the air through the vent 27 as shown in FIG. 3. Coolant flow is controlled to lower the cauldron temperature to approximately 16° C. as determined from the thermocouple 108 over the thermocouple leads 34 to the microprocessor. The microprocessor/controller 30 contains a reference junction for the thermocouple 108.

When the pressure detected by the microprocessor/controller 30 from the pressure transducer 89 stabilizes below the preselected pressure and the temperature detected from the thermocouple 108 is approximately 16° C., the vacuum pump 50 and EVAC light 214 are turned off. The pressure measured by the pressure transducer 89 in the manifold 16 at the time the vacuum pump is turned off is then read by the microprocessor/controller 30 and used as the zero level for subsequent pressure readings and calculations. The pressure transducer 89 may be a Celesco Model PLC manufactured by Transducer Products, Inc., 7800 Deering Ave., Canoga Park, Calif. A zero to 500 psi range was selected for use in the specific construction described herein.

The outputs from the pressure transducer 89 and the thermocouple 108 are amplified and fed to analog/digital converters. The digitized outputs are then read by the microprocessor part of the microprocessor/controller 30.

Before the vacuum pump 50 is turned off, the microprocessor/controller 30 activates the solenoid valve that closes the port 72 connected to the vacuum pump.

The microprocessor/controller 30 next activates the solenoid valve controlling opening of the port 74 to permit fluorocarbon fluid to flow through the fluorocarbon fill line 20 into the manifold 16 and thence into the bubble cauldron 10 through the fluorocarbon transfer line 18.

When the signal from the exclusive OR-gate 510 in the thermistor circuitry, FIG. 5, goes low, the microprocessor/controller 30 activates the solenoid to close the port 74 connected to the fluorocarbon fluid fill line. At the same time the microprocessor/controller 30 activates the solenoid 24 to disable the cooling mode at the switch 208 and enable the bellows displacement pump 60 system by activating the solenoid to open the port 76 to the pressure line 62. The microprocessor/controller 30 then activates the heating coils 104 through the heating line 36 to raise the bulk temperature of the fluid in the cauldron 10 to the value previously set by the operator by use of the switch 204. A bus 40 from the microprocessor/controller 30 to the ribbon connectors 122 on the printed circuit board 110 is then activated to energize the device 100 under test.

Figure 6:
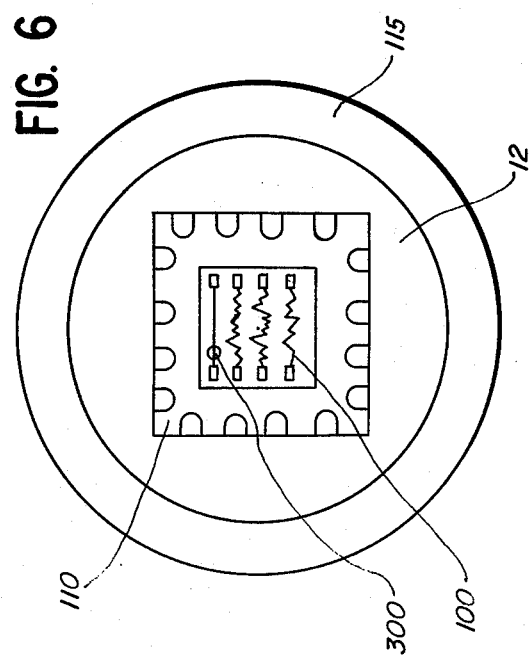
FIG. 6 is a magnified schematic representation of a device under test as seen in the bubble cauldron through a microscope.
Figure 6:
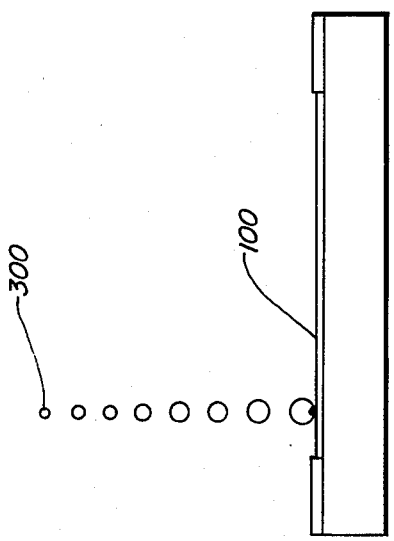

With the cauldron 10 full and heated to the indicated ambient temperature and the device 100 under test activated, the system is now ready for hot spot detection. An operator uses the switch 64 to decrease the pressure in the cauldron 10 until boiling is seen from the device 100 under test through the microscope 116. The boiling may be detected by direct observation of the device 100 under test in the microscope 116. Alternatively, the image may be viewed by means of a remote TV or other remote means. When boiling is seen, the switch 64 is used to increase the pressure on the fluid until all boiling is terminated except that from the last spot or spots to stop boiling, that is, the hottest spot or spots. At this point the bubble sizes will be small, and the appearance of the device 100 under test will be as indicated in idealized view in FIG. 6, where a single bubble stream 300 is indicated. An elevation view of the bubble field rising from the device 100 may be substantially as indicated in FIG. 6A. The operator may now slowly increase the pressure until the bubble stream 300 arising from the device 100 is just quenched. At this time he may activate a hold switch 216 on the control panel of the microprocessor/controller 30, and the microprocessor/controller 30 will then store signals indicative of the pressure from the transducer line 88 and the bulk liquid temperature from the thermocouple line 34. The data may be displayed on a display 218 on the control panel, as selected by a switch 220. The nucleate boiling point of the fluorocarbon selected with a fluid select switch 222 may also be read out of tables stored in the memory of the microprocessor/controller 30.

A precise determination of the hot spot temperature may now be made with the whirligig 130. The whirligig, which is described in detail in the concurrently filed application, is a combined heater/thermocouple. A hot spot 132 is provided at the position where the thermocouple wires cross. The thermocouple provides a continuous measurement of the hot spot temperature.

To use the whirligig 130, the temperature of the hot spot is increased until boiling from the hot spot is observed with the pressure maintained at the pressure where boiling was just quenched from the device 100. Because of liquid superheating effects boiling will ordinarily commence at a temperature higher than the boiling point of the liquid. Superheating effects are avoided in the present application by first observing the presence of boiling and then raising the pressure or lowering the temperature until boiling just ceases. Thus, in the present application of the whirligig 130, the temperature of the hot spot 132 is first raised to the point where boiling commences and then lowered to the point where observation of the bubble stream arising from the hot spot 132 shows that nucleate boiling has just been quenched. The temperature of the hot spot 132 is then recorded from the whirligig 130 by the microprocessor/controller 30. At the same time, the heating current in the whirligig 130 is also measured. Subsequently, after the cauldron 10 has been evacuated of fluid, the whirligig 130 may be rerun in air with the previously observed heating current, and the hot spot 132 temperature in air measured by the whirligig. This temperature will then be an approximation of the air temperature of the hot spot on the device being tested. Of course means 800, indicated symbolically in FIG. 3, which sense the presence of boiling other than optically also fall within the scope of the present invention.

It is not, of course, necessary to run the whirligig 130 in fluid and in air on each and every occasion. Conversion tables may be made up and stored in the microprocessor/controller 30 to relate liquid boiling points at various pressures to equivalent hot spot temperatures in air. Alternatively, tables may be compiled from experimental determinations of comparative liquid/air device temperatures where device temperatures are determined by lower resolution techniques.

It will, of course, be understood that modification of the present invention in its various aspects would be apparent to those skilled in the art, some being apparent only after study and others being a matter of routine design. For example, the use of any particular coolant is not a necessary feature of the invention. Various other coolants, such as circulating ice water or liquid $N_2$, could be used just as well. Alternatively, a closed cycle refrigeration system may be used for cooling. The particular form of the bubble cauldron 10 and its construction are also not necessary features of the invention. Persons skilled in the art will conceive of other forms of containers which will also serve the purpose of hot spot detection. Although the present disclosure emphasizes optical detection of bubble streams, it is also possible to detect such streams acoustically or electrically, for example by capacitance means, or in other ways not specifically disclosed herein. As such, the scope of the invention should not be limited by the particular embodiment and specific construction herein described, which should be defined only by the appended claims and equivalents thereof.

What is claimed is:

1. An ebulliometric hot spot detector for detecting hot spots on a powered electronic device, comprising:
   container means for containing an ebulliometric liquid and a powered electronic device within a chamber, with said electronic device supported submerged in said ebulliometric liquid,
   power means for applying power to said electronic device,
   pressurizing means for establishing and varying pressure in the ebulliometric liquid in said chamber,
   detector means for detecting the onset and termination of bubbling of said ebulliometric liquid in said chamber from the surface of said integrated circuit as said pressure is varied, including means for detecting the location of the sources of said bubbling, and
   output means responsive to said pressure for generating and displaying a signal indicative of said pressure at the time of said termination of bubbling.

2. An ebulliometric hot spot detector according to claim 1 including an ebulliometric liquid comprising a fluorocarbon liquid.

3. An ebulliometric hot spot detector according to claim 1 wherein said container means includes a bubble cauldron comprising:
   a container capable of containing said ebulliometric liquid at pressures substantially higher than atmospheric,
   ambient temperature control means for raising and lowering the internal temperature of said ebulliometric liquid contained in said cauldron,
   viewing means for optically coupling the interior of said cauldron to the outside of said cauldron, and mounting means for supporting said integrated circuit within said bubble cauldron in a position viewable from outside said bubble cauldron by use of said viewing means.

4. An ebulliometric hot spot detector according to claim 3 wherein said power means includes a printed circuit board having at least a portion situated within said bubble cauldron and including means for making electrical connections to said printed circuit board externally to said bubble cauldron.

5. An ebulliometric hot spot detector according to claim 3 including a reservoir for containing said ebulliometric liquid, and means for filling said bubble cauldron from said reservoir and emptying said bubble cauldron into said reservoir.

6. An ebulliometric hot spot detector according to claim 5 wherein said means for filling includes at least one thermistor liquid level detector.

7. An ebulliometric hot spot detector according to claim 1, wherein said container means including a pressure transducer disposed within said chamber.

8. An ebulliometric hot spot detector according to claim 7 wherein said pressurizing means includes a bellows pump.

9. An ebulliometric hot spot detector according to claim 8 wherein said pressurizing means further includes a stepping motor, and said bellows pump is operated by said stepping motor.

10. An ebulliometric hot spot detector according to claim 1 wherein said detector means includes a microscope.

11. An ebulliometric hot spot detector according to claim 1 wherein said viewing means includes remote television.

12. An ebulliometric hot spot detector according to claim 1 including boiling point determination means, responsive to said signal from said output means, for determining the boiling point temperature of said ebulliometric liquid at said pressure at the time of said termination of boiling.

13. An ebulliometric hot spot detector according to claim 12 wherein said boiling point determination means includes a heatable point immersed in said ebulliometric liquid within said chamber, means for determining the temperature of said heatable point, means for raising and lowering the temperature of said heatable point, and means for detecting the onset and cessation of bubbling from said heatable point.

14. An ebulliometric hot spot detector according to any one of claims 1 to 10, 13, 11 and, 12 wherein said hot spot detector further comprises a microprocessor/control means for controlling any of the means for filling, power means, pressurizing means, detection means, and boiling point determination means, and wherein any of said means for filling, power means, pressurizing means, detection means and boiling point determination means operate under control of said microprocessor/control means.

15. An ebulliometric hot spot detector for detecting hot spots on an integrated circuit comprising:

an ebulliometric liquid,
container means for containing said ebulliometric liquid and said integrated circuit within a chamber, with said integrated circuit supported submerged in said ebulliometric liquid,
power means for applying power to said integrated circuit,
pressurizing means for establishing and varying pressure in said ebulliometric liquid in said chamber,
detection means for detecting the onset and cessation of bubbling of said ebulliometric liquid in said chamber from the surface of said integrated circuit as said pressure is varied, including means for detecting the location of at least one of the sources of said bubbling, and
temperature determination means responsive to said pressure for determining the temperature of at least one of the sources of said bubbling.

16. An ebulliometric hot spot detector according to claim 15 wherein said pressurizing means includes a pump comprising:

housing means for cleanly containing said ebulliometric liquid under positive and negative gauge pressures,
connecting means for carrying said ebulliometric liquid from said housing means to said apparatus,
a bellows having an interior chamber and an external face, said external face housing means to contain said liquid under positive and negative gauge pressures separate from said interior chamber of said bellows, and
driving means for expanding and contracting said bellows.

17. An ebulliometric hot spot detector according to claim 16 wherein said interior chamber of said bellows contains gas at a predetermined pressure different from atmospheric.

18. An ebulliometric method for detecting hot spots on a powered electronic device comprising the steps of:
submerging a powered electronic device in ebulliometric fluid,
producing such pressure in said ebulliometric fluid as to produce boiling from said device,
increasing said pressure until said boiling ceases, and observing boiling sites on said device.

19. An ebulliometric method according to claim 18 including the step of determining the location on said device of at least one boiling source as boiling from said source ceases.

20. An ebulliometric method according to claim 18 including the step of determining the pressure at which boiling from at least one boiling source ceases.

21. An ebulliometric method according to claim 18 including the step of determining the temperature of at least one boiling source when boiling ceases thereat.

22. An ebulliometric method according to claim 18 including the step of determining from the pressure at which boiling ceases the temperature at which at least one of the sources of bubbling operates in air.

* * * * *

UNITED STATES PATENT AND TRADEMARK OFFICE
CERTIFICATE OF CORRECTION

PATENT NO. : 4,466,746
DATED : August 21, 1984
INVENTOR(S) : Robert D. Hancock and Kenneth F. Hollman It is certified that error appears in the above-identified patent and that said Letters Patent is hereby corrected as shown below:

Column 3, line 63, after "spot" insert --device--.

Column 5, line 23, after "side" insert a comma (,).

Column 7, line 7, change "110" to --100--.

Column 7, line 45, change "plane" to --panel--.

Column 8, line 42, change "therfore" to --therefore--.

Column 8, line 50, change "about" to --above--.

Column 9, line 18, change "the" to --a--.

Column 9, line 21, change "diamter" to --diameter--.

Column 9, line 60, change "aong" to --along--.

Column 14, line 48 (Claim 1), change "integrated circuit" to --powered electronic device--.

Column 16, line 26 (Claim 16), change "apparatus" to --chamber--.

Column 16, line 28 (Claim 16), after "face" second occurrence, insert --cooperating with said--.

Signed and Sealed this

Sixteenth Day of April 1985

[SEAL]

Attest:

DONALD J. QUIGG

Attesting Officer  Acting Commissioner of Patents and Trademarks

UNITED STATES PATENT AND TRADEMARK OFFICE
CERTIFICATE OF CORRECTION

PATENT NO. : 4,466,746

DATED : August 21, 1984

INVENTOR(S) : Robert D. Hancock and Kenneth F. Hollman

It is certified that error appears in the above-identified patent and that said Letters Patent is hereby corrected as shown below:

Column 15, line 1 (Claim 3), change "integrated circuit" to --powered electronic device--.

Signed and Sealed this

Fourth Day of June 1985

[SEAL]

Attest:

DONALD J. QUIGG

Attesting Officer    Acting Commissioner of Patents and Trademarks